United States Patent [19]

Weber et al.

[11] 4,414,419

[45] Nov. 8, 1983

[54] STABILIZATION OF ALDEHYDES

[75] Inventors: Jürgen Weber, Oberhausen; Volker Falk, Voerde; Claus Kniep, Oberhausen, all of Fed. Rep. of Germany

[73] Assignee: Ruhrchemie Aktiengesellschaft, Fed. Rep. of Germany

[21] Appl. No.: 115,781

[22] Filed: Jan. 28, 1980

[30] Foreign Application Priority Data

Feb. 12, 1979 [DE] Fed. Rep. of Germany ....... 2905267
May 3, 1979 [DE] Fed. Rep. of Germany ....... 2917789

[51] Int. Cl.$^3$ ..................... C07C 47/058; C07C 47/02
[52] U.S. Cl. ................................................... 568/421
[58] Field of Search ............... 568/421, 304, 422, 423; 260/601 R

[56] References Cited

U.S. PATENT DOCUMENTS

| | | | |
|---|---|---|---|
| 2,237,092 | 4/1941 | Swain et al. | 568/422 |
| 3,168,573 | 2/1965 | Butter | 568/422 |
| 3,257,162 | 6/1966 | Cox | 568/421 |
| 3,562,344 | 2/1971 | Berkowitz et al. | 568/421 |
| 3,849,498 | 11/1974 | Sato et al. | 568/421 |

OTHER PUBLICATIONS

Bogert et al., "Drugs and Cosmetic Industry" Apr. 1933, pp. 312 and 332–338.
Bogert et al., "Drug and Cosmetic Industry", Jun. 1933, pp. 513 and 533–540.
Fiore et al., "The American Perfume and Essential Oil Review" Jul. 1944, pp. 33–35.

*Primary Examiner*—Werren B. Lone
*Attorney, Agent, or Firm*—Jordan B. Bierman; Linda Bierman

[57] ABSTRACT

Aldehydes having 3 to 14 carbon atoms are stabilized against polymerization and autocondensation by the addition thereto of triethanolamine or dimethylethanolamine in an amount at least 10 ppm (based on the amount of aldehyde) and preferably 20 to 100 ppm.

15 Claims, No Drawings

STABILIZATION OF ALDEHYDES

This application claims the priority of German application Nos. P 29 05 267.3 and P 29 17 789.7 filed Feb. 12, 1979 and May 3, 1979, respectively.

The invention relates to the stabilization of aldehydes having 3 to 14 carbon atoms against polymerization and autocondensation.

Such aldehydes have a tendency to spontaneously undergo polymerization and autocondensation. They have a tendency to form a cyclic trimeraldehyde (trialkyltrioxane) of the general formula

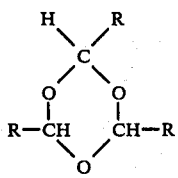

(where RCHO is the formula of the initial aldehyde and R represents an alkyl radical), and to form aldol condensation products by autocondensation. The ring-forming polymerization of isobutyraldehyde mainly produces 2,4,6-triisopropyl-1,3,5-trioxane. The autocondensation of isobutyraldehyde leads to the aldol condensation product 2,6-diisopropyl-5,5-dimethyl-1,3-dioxan-4-ol. The ring-forming polymerization of aldehydes is catalyzed by various acid reagents such as sulphuric acid, hydrochloric acid, hydrogen fluoride, boron trifluoride and aluminum chloride. Under the action of such acidic compounds the polymerization of the aldehydes occurs spontaneously and leads within a few minutes to crystalline trimeraldehydes. Even the small amounts of carboxylic acids formed by the oxidation of the aldehydes in the presence of atmospheric oxygen are sufficient for catalyzing the trimer formation. The trimerization of isobutyraldehyde is catalyzed particularly by chlorine, bromine, phosphorus pentoxide, hydrogen chloride, oxygen and zinc chloride. Trimerization of isobutyraldehyde also occurs under the action of UV light. Also in the presence of alkali, derived for example from the containers in which the isobutyraldehyde is stored, autocondensation of isobutyraldehyde to form 2,6-diisopropyl-5,5-dimethyl-1,3-dioxan-4-ol occurs even at 5° to 10° C. In addition, low temperatures, i.e. temperatures of about 0° C. and below, promote the polymerization of aliphatic aldehydes.

On account of its conversion into higher molecular weight compounds, in particular under the action of oxygen or UV light or alkaline-reacting substances, isobutyraldehyde cannot be stored for an indefinite period of time. Although in fact the polymerization and autocondensation products of isobutyraldehyde decompose further at elevated temperature, their formation nevertheless prevents the unlimited technical use of the aldehyde.

Trimerization and autocondensation of aldehydes can be prevented for a limited period of time if the aldehydes are highly pure. The purification operations required are however so costly that they are not practicable for the commercial preparation of aldehydes. Also, addition of a solution of diphenylamine in ethanol to aldehydes suppresses polymerization but is not reliable for this purpose over a prolonged period of time.

Attempts have been made to prevent the formation of higher molecular weight products from isobutyraldehyde. Polymerization and autocondensation reactions can be prevented by the addition of suitable substances. In practice these substances are subject to a whole range of requirements that have to be satisfied if the aldehyde is to be used without any restriction in a very wide variety of applications. One such requirement is that the substance in question must be effective for a long period of time in low concentrations and furthermore must not interfere in the processing of the aldehyde by chemical conversions.

Mercaptobenzimidazole and 2,2-methylene-di-(4-methyl-6-tert.-butylphenol) have been described as stabilizers for isobutyraldehyde. It has been found, however, that both of these stabilizers are not active for a sufficient length of time.

An object of the invention is to provide stabilizers that prevent, even in low concentration, polymerization and autocondensation reactions of aldehydes for as long a period of time as possible.

It has now surprisingly been found that aldehydes with up to 14 carbon atoms can be effectively stabilized against polymerization and autocondensation by adding triethanolamine or dimethylethanolamine to them. Accordingly, the present invention provides a process for stabilizing an aldehyde having 3 to 14 carbon atoms against polymerization and autocondensation comprising adding triethanolamine or dimethylethanolamine to the aldehyde.

The invention also provides a composition comprising an aldehyde having 3 to 14 carbon atoms and triethanolamine or dimethylethanolamine, the aldehyde being stabilized against polymerization and autocondensation by the triethanolamine or dimethylethanolamine.

Examples of aldehydes of the aforementioned molecular size are: propanal, isobutyraldehyde, n-pentanal, and dimethylhexanal. Further examples are, in particular, higher aldehydes containing 8 to 14 carbon atoms, such as n-octylaldehyde, n-nonyl-aldehyde, n-decylaldehyde, undecylaldehyde, lauraldehyde, methylnonylacetaldehyde (MNA), tridecylaldehyde, and myristylaldehyde, which are used on a large scale in the preparation of synthetic perfumes and fragrances. In this connection, it is therefore important that the substances added to prevent polymerization are not only highly effective, but also do not have any negative effect on the nature or character of the perfumes prepared therefrom. It has surprisingly been found that triethanolamine and dimethylethanolamine are highly effective and meet these requirements in an outstanding manner. Neither amine interferes in the further processing of the aldehydes to form secondary products. It should be noted in particular that triethanolamine and dimethylethanolamine, although they react in an alkaline manner, do not catalyze the aldol condensation of the aldehydes.

These stabilizers are effective even in very low concentrations. As little as 10 ppm (based on the aldehyde) of the amines prevent the formation of high molecular weight compounds over a period of at least several weeks, e.g., in the case of isobutyraldehyde under the action of oxygen, for a period of 30 weeks. In general, it is preferred that the stabilizers be used in amounts of 20 to 100 ppm (based on the aldehyde). In such a concentration, the stabilizers prevent the formation of the trimer or autocondensation aldol product during storage of the aldehyde, even at low temperatures, without any further measures or precautions and for a period of at least several months, depending on the aldehyde, and one year in the case of isobutyraldehyde.

Triethanolamine and dimethylethanolamine are soluble in the aforementioned aldehydes and can thus be used without solvents. The amines are preferably added in specified amounts while stirring and at such a rate that no local overheating occurs. The following examples are intended to illustrate the present invention in greater detail.

EXAMPLE 1

Tests on the stabilization of isobutyraldehyde were carried out in polyethylene-lined containers. The containers were stored in the open and thus subjected to variable temperatures. As stabilizer, either triethanolamine or dimethylethanolamine in a concentration of 20 to 100 ppm was used. The polymer content was determined by gas chromatography every 4 weeks. Errors were excluded by a system of double determinations. The results are given in the Table 1 below.

| Stabilizer (concentration) | Amount of material used | Trimer content (%) as a function of the storage time under comparable conditions | | | | | | |
|---|---|---|---|---|---|---|---|---|
| | | 5 weeks storage time | 10 weeks storage time | 20 weeks storage time | 30 weeks storage time | 40 weeks storage time | 50 weeks storage time | 60 weeks storage time |
| Mercaptobenzimidazol (100 ppm) | 0.02 | 0.36 | 0.59 | — | — | — | — | — |
| Dimethylethanolamine (100 ppm) | 0.02 | 0.02 | 0.02 | 0.02 | 0.03 | 0.04 | 0.07 | 0.10 |
| Dimethylethanolamine (20 ppm) | 0.02 | 0.02 | 0.02 | 0.02 | 0.04 | 0.06 | 0.10 | 0.17 |
| Triethanolamine (100 ppm) | 0.02 | 0.02 | 0.02 | 0.02 | 0.02 | 0.02 | 0.05 | 0.09 |
| Triethanolamine (20 ppm) | 0.02 | 0.02 | 0.02 | 0.02 | 0.02 | 0.02 | 0.06 | 0.12 |
| No stabiliser | 0.02 | 0.86 | 2.60 | 4.80 | 7.00 | 7.60 | 7.70 | 9.00 |

EXAMPLE 2

20 ppm (based on the aldehyde) of triethanolamine or diphenylamine was added to n-dodecanal (lauraldehyde) and the aldehyde was stored in aluminum containers some of which were kept at 0° C. and some of which were kept at 20° C.

The aldehyde content was monitored by determining the carbonyl number (CON) after 1, 3, 6, 9 and 14 weeks. Errors were eliminated by a system of double determinations. The results are given in Table 2.

TABLE 2

| Stabilizer | Start of Test | After 1 weeks | After 3 weeks | After 6 weeks | After 9 weeks | After 14 weeks |
|---|---|---|---|---|---|---|
| Temperature: 0° C. | | | | | | |
| None | 288 | 198 | 121 | 73 | 50 | 33 |
| Diphenylamine in ethanol | 288 | 282 | 270 | 230 | 148 | 100 |
| Triethanolamine | 288 | 287 | 286 | 286 | 284 | 273 |
| Temperature: 20° C. | | | | | | |
| None | 288 | 286 | 284 | 275 | 275 | 270 |
| Diphenylamine in ethanol | 288 | 287 | 283 | 282 | 282 | 274 |
| Triethanolamine | 288 | 287 | 287 | 286 | 283 | 281 |

What we claim is as follows:

1. A process for stabilizing a saturated aliphatic aldehyde having 3 to 14 carbon atoms against polymerization and autocondensation comprising adding an effective amount of triethanolamine or dimethylethanolamine to said aldehyde.

2. A process according to claim 1 wherein said triethanolamine or dimethylethanolamine is added to said aldehyde in an amount of at least 10 ppm based on said aldehyde.

3. A process according to claim 2 wherein said amount is 20 to 100 ppm.

4. A process according to claim 1 wherein said aldehyde is isobutyraldehyde.

5. A process according to claim 1 wherein said aldehyde has 8 to 14 carbon atoms.

6. A process according to claim 1 wherein said aldehyde is n-octylaldehyde, n-nonylaldehyde, n-decylaldehyde, undecylaldehyde, lauraldehyde, methyl nonylacetaldehyde, tridecylaldehyde or myristylaldehyde.

7. A composition comprising a saturated, aliphatic aldehyde having 3 to 14 carbon atoms and an effective amount of triethanolamine or dimethylethanolamine, the aldehyde being stabilized against polymerization and autocondensation by the triethanolamine or dimethylethanolamine.

8. A composition according to claim 7 comprising at least 10 ppm of the triethanolamine or dimethylethanolamine based on said aldehyde.

9. A composition according to claim 8 comprising 20 to 100 ppm of the triethanolamine or dimethylethanolamine based on said aldehyde.

10. A composition according to claim 7 consisting essentially of said triethanolamine or dimethylethanolamine and said aldehydes.

11. A composition according to claim 7 wherein said aldehyde is isobutyraldehyde.

12. A composition according to claim 7 wherein said aldehyde has 8 to 14 carbon atoms.

13. A composition according to claim 12 wherein said aldehyde is n-octylaldehyde, n-nonylaldehyde, n-decylaldehyde, undecylaldehyde, lauraldehyde, methylnonylacetaldehyde, tridecylaldehyde or myristylaldehyde.

14. A process according to claim 1 wherein said amount is at least 20 ppm based on said aldehyde.

15. A composition according to claim 7 wherein said amount is at least 20 ppm based on said aldehyde.

* * * * *